United States Patent [19]

Langdon-Orr et al.

[11] Patent Number: 5,101,815

[45] Date of Patent: Apr. 7, 1992

[54] SPLINTING METHOD, SPLINT AND STRAP

[76] Inventors: Cheryl R. Langdon-Orr; Graham F. Orr, both of 40 Hackenberg Road, Glenorie, Australia, 2157; Barry J. Collins, 9 Brenda Court, North Rocks, Australia, 2151

[21] Appl. No.: 458,649

[22] PCT Filed: Jul. 1, 1988

[86] PCT No.: PCT/AU88/00233

§ 371 Date: Feb. 26, 1990

§ 102(e) Date: Feb. 26, 1990

[87] PCT Pub. No.: WO89/00036

PCT Pub. Date: Jan. 12, 1989

[30] Foreign Application Priority Data

Jul. 2, 1987 [AU] Australia .................. PI2847

[51] Int. Cl.⁵ .................. A61F 5/04; A61F 5/37
[52] U.S. Cl. .................. 602/12; 128/876; 128/DIG. 20; 602/23
[58] Field of Search .................. 128/87 R, 869–876, 128/78, DIG. 20; 5/82 R

[56] References Cited

U.S. PATENT DOCUMENTS

| | | | |
|---|---|---|---|
| 1,221,289 | 4/1917 | Clough | 128/87 R |
| 1,577,712 | 3/1926 | Graham | 128/85 |
| 2,766,751 | 10/1956 | Topa | 128/870 |
| 3,823,712 | 7/1974 | Morel | 128/87 R |
| 3,868,952 | 3/1975 | Hutton | 128/78 |
| 3,886,606 | 6/1975 | Bradford | 5/82 |
| 3,976,062 | 8/1976 | Cox | 128/87 R |
| 3,982,531 | 9/1976 | Shaffer | 128/DIG. 20 |
| 3,993,056 | 11/1976 | Rabischong | 128/DIG. 20 |
| 4,169,467 | 10/1979 | Rabischong | 128/DIG. 20 |
| 4,649,907 | 3/1987 | Whitehead et al. | 128/84 C |
| 4,708,131 | 11/1987 | Kendrick | 128/85 |
| 4,715,362 | 12/1987 | Scott | 128/75 |
| 4,852,587 | 8/1989 | Share | 128/873 |

FOREIGN PATENT DOCUMENTS

| | | |
|---|---|---|
| 137259 | 4/1985 | European Pat. Off. |
| 367368 | 1/1923 | Fed. Rep. of Germany |
| 958426 | 12/1947 | France |
| 88014944 | 4/1988 | PCT Int'l Appl. |
| 327628 | 4/1930 | United Kingdom |

Primary Examiner—Robert A. Hafer
Assistant Examiner—Michael Brown
Attorney, Agent, or Firm—Wegner, Cantor, Mueller & Player

[57] ABSTRACT

The present invention discloses a method of splinting and a splint (1) movable between a folded transport configuration and an extended operational configuration. Straps (10, 20 and 80) to bind the splints to a patient's body are also disclosed. The invention is particularly applicable to splinting broken femurs, however, upper arm, lower arm, lower leg and other fractures can also be immobilized. The straps (10, 20 and 80), splints (1) and any securing devices such as buckles (13) or pegs (82) can be accommodated in a convenient carry pouch or bag (85).

5 Claims, 12 Drawing Sheets

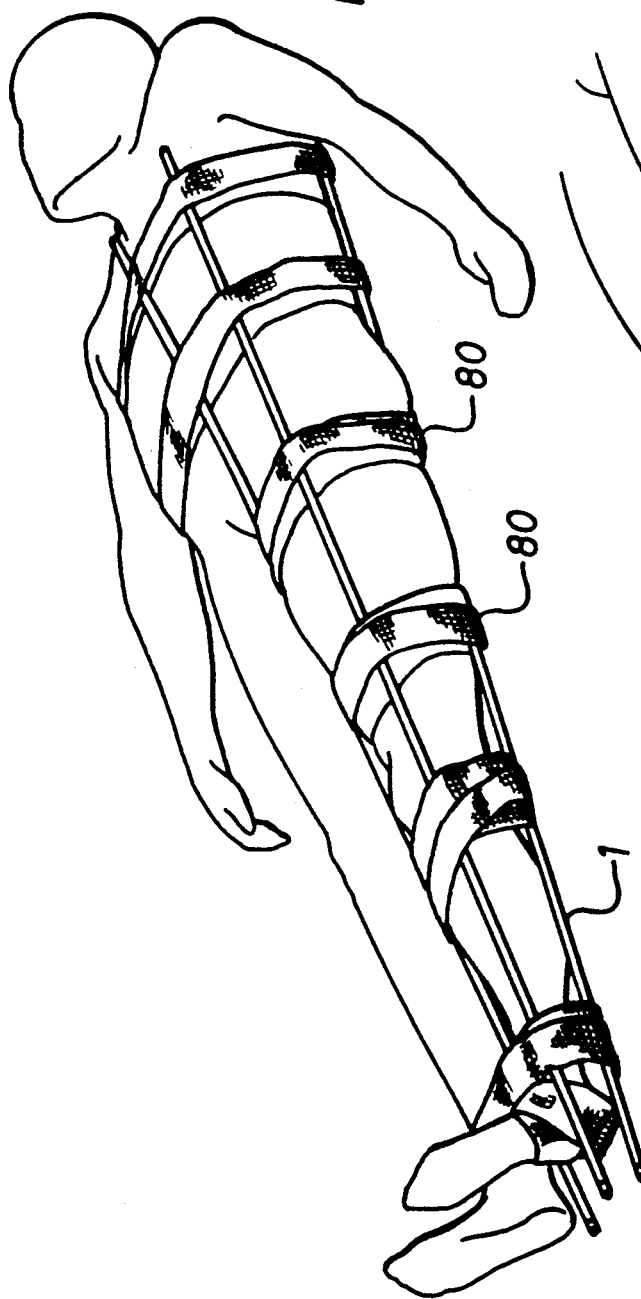
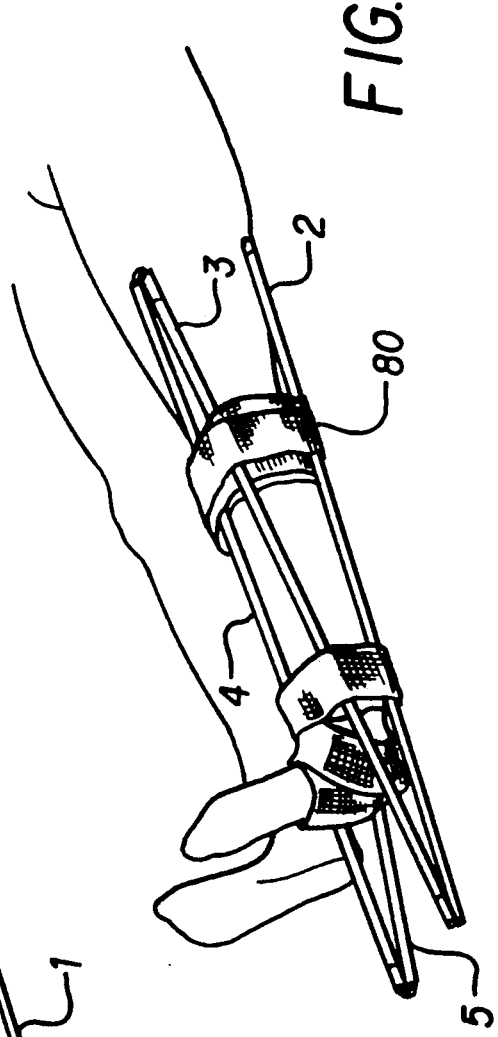

SPLINTING METHOD, SPLINT AND STRAP

The present invention relates to a method of splinting and to splints, splint securing straps, and first aid kits for fractures. Whilst the present application finds particular application to the splinting of fractured femurs, many aspects of the present invention are not limited thereto.

TECHNICAL FIELD

Fractured femurs often arise as a result of motor bike accidents, and also from military accidents and wounds such as those generated by Claymore mines and bullet wounds to the thigh. Irrespective of whether the fractured femur arises as a result of civilian or military endeavors, there is no really effective practical method of safely splinting the fracture to enable the patient to be transported from the side at which the fracture occurred, to hospital. Clearly the purpose of any splint is to immobilize the fracture, however, the main problem with fractured femurs appears to be preventing rotation of the leg about a longitudinal axis passing through the leg.

BACKGROUND ART

One prior art method of splinting a femur fracture is to use a single rigid splint, such as a broomstick, which extends between the armpit and ankle of the patient. The patient's leg is bound to the broomstick and then the patient is transported to hospital on a stretcher or the like. Whilst in some circumstances this method may be satisfactory for distal fractures (that is those away from the pelvis and therefore adjacent the knee), this prior art method is not very satisfactory for proximal fractures (those which are near the pelvis).

An alternative arrangement is the so called Thomas splint which applies a frame to the torso of the patient and also applies longitudinal traction to the lower leg. This splint is a relatively expensive appliance and is substantially bulky. Therefore although the splint may be of some use for ambulance officers, for example, transporting an elderly patient to hospital after a fall where the nature of the injuries are known before the ambulance departs from its base, this splint is of little use as a first aid measure in emergency situations such as motor vehicle accidents or military accidents/wounds.

A further device is the so called Mast suit which comprises a pair of trousers into which the legs of the patient are inserted. The trousers are then inflated so as to form a rigid enveloping structure. This suit suffers from a number of disadvantages in that firstly the legs of the patient need to be held apart. Thus this suit is not able to be used with the Thomas splint or the other above described conventional splints where the "good" leg is used in the splinting arrangement. Furthermore, the Mast suit pushes blood back into the upper part of the body and in some circumstances this can be disadvantageous to the patient.

As a consequence of the above described problems with splinting, it sometimes happens that first aid personnel apply plaster to the leg of the patient at the site of the accident before moving the patient. This has two major disadvantages. Firstly it is extremely difficult in emergency situations such as arise as a result of military wounds where the patient may well be under fire, in darkness, or the like. Secondly, once the plastered patient has been transported to hospital, the plaster must then be removed before further treatment is able to be commenced. This is a painful and time consuming procedure and therefore to be avoided if possible.

OBJECTS OF THE INVENTION

It is the object of the present invention to provide a method of splinting a patient having a leg with a fracture of the femur. A further object of the present invention is to provide a splint which is able to be folded and therefore able to be carried conveniently in a first aid kit, or the like, so as to be readily available in emergency situations. A still further object of the present invention is to provide a splint securing strap for use with the splint of the present invention, or conventional splints, and which is able to be applied with ease so as to result in a secure job. A still further object of the present invention is to provide a first aid kit incorporating foldable splints and splint securing straps.

SUMMARY OF THE INVENTION

According to a first aspect of the present invention there is disclosed a method of splinting a patient having a leg with a fracture of the femur, said method comprising the steps of straightening said leg if necessary, positioning three substantially rigid splints to extend between substantially the ankle of said leg and the armpit region of said patient, arranging said splints to lie at the vertices of a triangle when said leg is viewed in transverse cross-section, and securing said splints so arranged to the body of said patient.

According to a second aspect of the present invention there is disclosed a foldable splint comprising four tubes which are able to be longitudinally aligned and abutted to form said splint, those ends of said tubes abutting another tube end when so aligned, having a mutually co-operative engagement means whereby said abutting tube ends can be engaged when so aligned to make said splint substantially rigid; and a flexible resilient member extending through the interior of said tubes and secured to the opposite end tubes of the aligned tubes, said flexible resilient member urging said tubes into engagement when said tubes are longitudinally aligned, and flexing to permit said tubes when dis-engaged to be folded to lie substantially alongside each other, each of said tubes being of substantially equal length and said length corresponding to the distance between wrist and elbow of an adult male.

According to another aspect of the present invention there is disclosed a splint securing strap comprising a pliant base strap having two ends, at least one splint receiving aperture formed in said base strap, and a hook means located adjacent one of said strap ends and engageable with said strap to form said strap into a loop having a length determined by the portion of said strap selected to be engaged with said hook means.

Preferably the location of the hook means is adjustable to provide adjustment of the loop length. Preferably the splint receiving apertures are formed by a second strap overlying at least a portion of the base strap and secured thereto intermediate the spaced apart locations. Alternatively an extended aperture can be used to receive a plurality of splints. Preferably the base strap is hollow and inflatable.

According to a further aspect of the present invention there is disclosed a first aid kit for fractures, said kit comprising a plurality of the above described splints and a plurality of the above described straps.

BRIEF DESCRIPTION OF THE DRAWINGS

Embodiments of the present invention will now be described with reference to the drawings in which:

FIG. 18 is a view similar to FIG. 7 but utilizing the straps of FIGS. 13-15, FIG. 19 is a perspective view illustrating an alternative lower limb splinting method.

BEST MODE FOR CARRYING OUT THE INVENTION

Figures 1, 2:
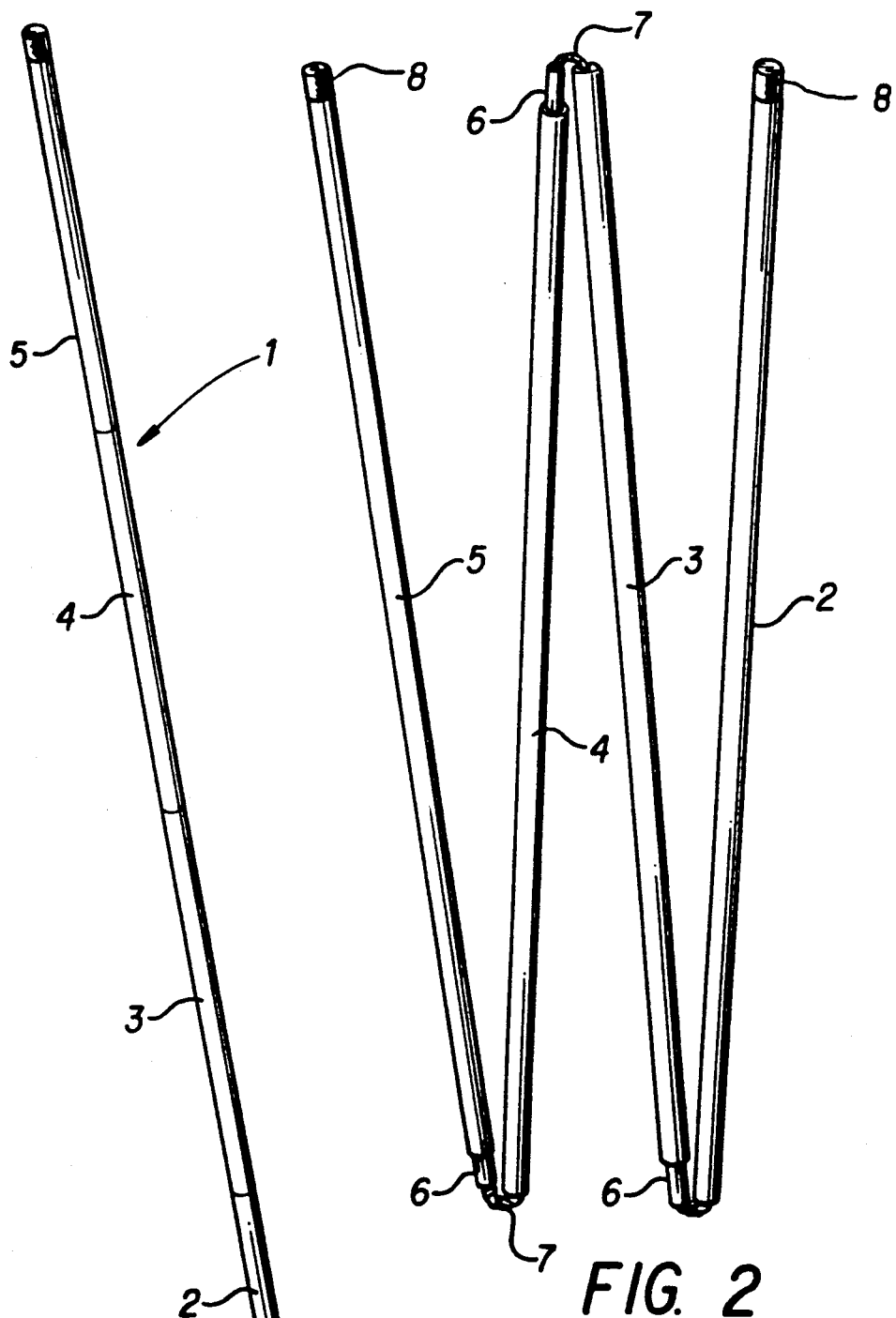
FIG. 1 is a perspective view of the splint of the preferred embodiment in the extended, operational configuration.
FIG. 2 is a perspective view, to an enlarged scale, of the splint of FIG. 1 in the folded transport configuration.
Figure 3:
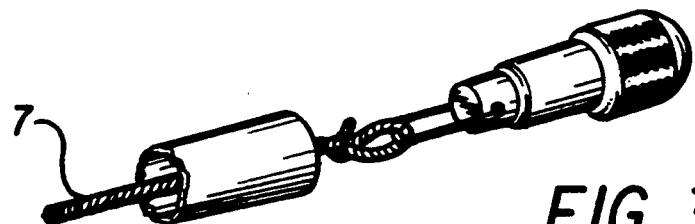
FIG. 3 is an expanded perspective view of one end of the splint of FIGS. 1 and 2.

Turning now to FIGS. 1 to 3, the splint 1 of the preferred embodiment is illustrated and is formed from four tubes 2-5. It will be apparent that tubes 2 and 5 are opposite end tubes whilst tubes 3 and 4 are intermediate tubes. As seen in FIG. 1, the splint 1 is in its extended, rigid, operational configuration.

However, as seen in FIG. 2 the splint 1 is able to be folded so as to be placed in a compact transport configuration.

As also seen in FIG. 2 a rod 6 is secured to one end of all the tubes other than tube 2 so as to form a means of inter-engaging the tubes 2-5. The rod 6 is hollow and has an outside or external diameter substantially equal to the internal diameter of the hollow tubes 2-5. The rods 6 are partially inserted within the tubes 2-5 and secured thereto by any conventional means such as blind rivets (not illustrated).

A flexible resilient filament 7, preferably formed from fabric covered rubber, extends between the opposite ends of tubes 2 and 5 and is secured thereto at end caps 8 as illustrated in FIG. 3. It will be apparent that the flexible filament 7 permits the tubes 2-5 to be folded into the transport configuration illustrated in FIG. 2. The tubes 2-5 must be bound together in this configuration by means of a restraint (not illustrated) such as a rubber band or tie string. When the restraint is released, the inclination of the filament 7 to be unstretched results in the tubes 2-5 being urged to longitudinally align themselves. It is then a relatively easy matter for each rod 6 to be inserted into the open adjacent end of the adjacent tube. In this way, the tubes 2-5 are converted into the operational configuration illustrated in FIG. 1.

Furthermore, because of the simplicity of the above described arrangement, the conversion can easily take place in the dark and under difficult conditions such as may be experienced by the military under fire.

Figure 4:
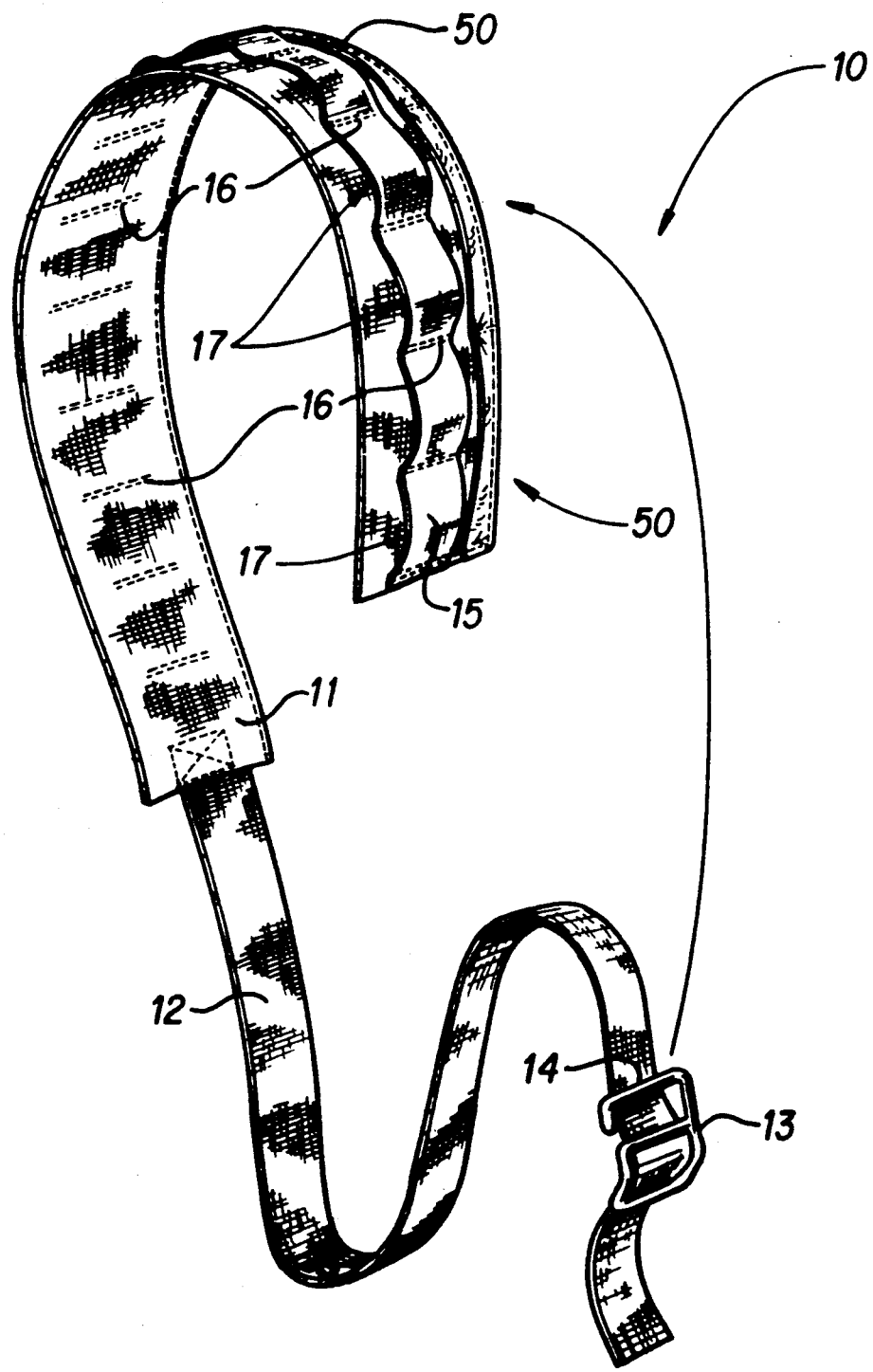
FIG. 4 is a perspective view of a first embodiment of a splint securing strap in accordance with the present invention.

Turning now to FIG. 4, a splint securing strap 10 for use with the splint 1 of FIGS. 1 and 2 (or with conventional splints such as a length of wood) is illustrated in FIG. 4. The strap 10 is formed from pliant strong material such as fabric webbing and comprises a base strap 11 having a narrower extension strap 12 secured thereto by any convenient means such as sewing. The free end of the extension strap 12 carries a buckle 13 which is able to be secured to the strap 12 at any adjustable location. The buckle 13 is provided with a hook 14.

Secured to one side of the base strap 11 is a securing strap 15 also formed from webbing. The strip 15 is secured at spaced apart locations 16 to the base strap 11 by any convenient means such as sewing so as to form a number of spaced apart apertures 17.

Preferably secured along one outer edge of the base strap 11 is an elongated pocket 50 the function of which will be described hereafter.

As schematically illustrated in FIG. 4 by means of the arrow, the hook 14 of the buckle 13 is able to be placed through any selected one of the apertures 17 so as to engage the hook 14 with the strip 15. In this way, a loop of selected predetermined length is formed. By sliding the extension strap through the buckle 13, the length of the loop can be adjusted.

Figures 5, 6:
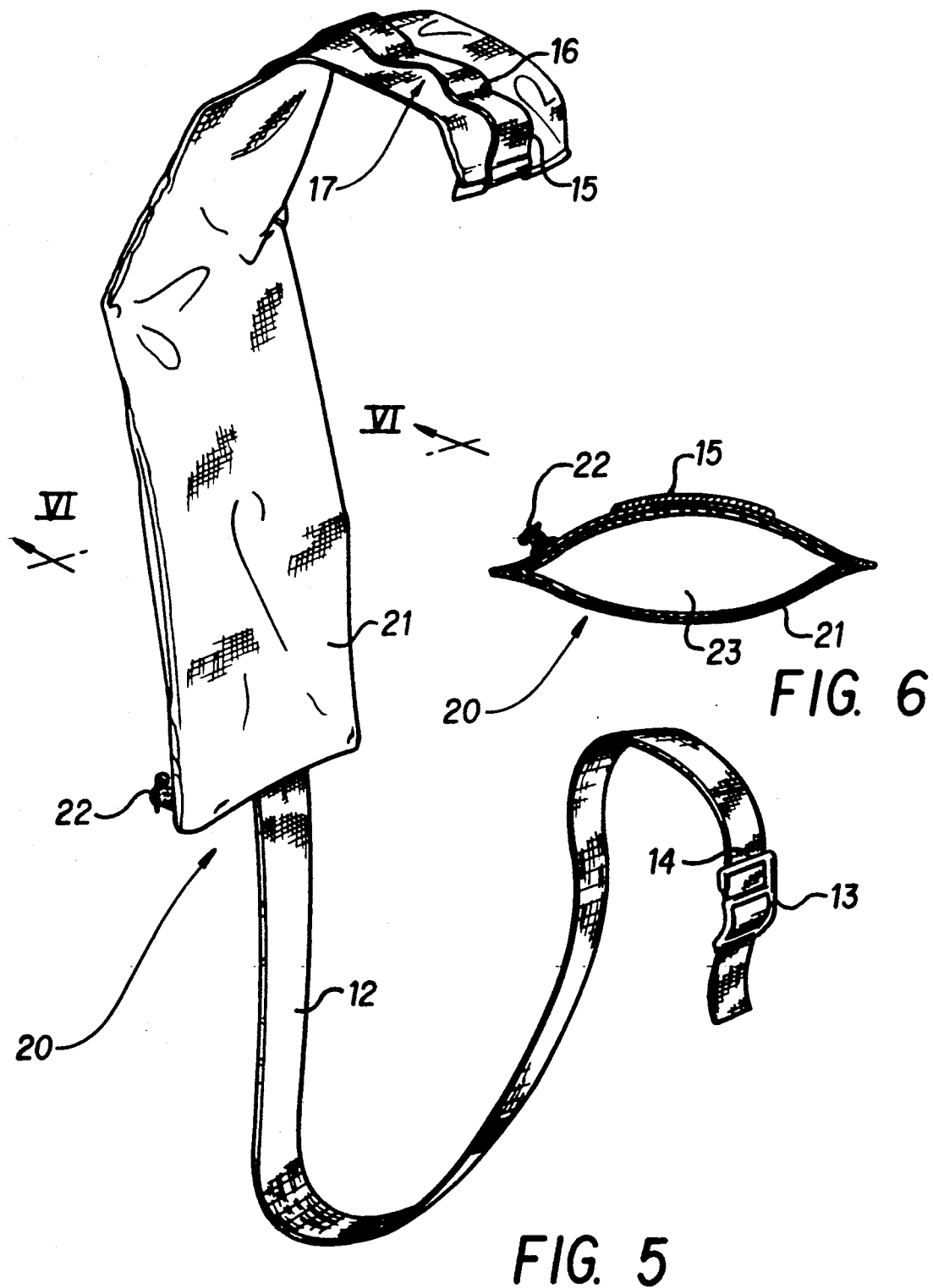
FIG. 5 is a view similar to FIG. 4 but of a second embodiment of a splint securing strap.
FIG. 6 is a cross-sectional view taken along the line VI—VI of FIG. 5 but illustrating the splint securing strap of FIGS. 5 and 6 in the inflated condition.

FIGS. 5 and 6 illustrate a second embodiment of a splint securing strap 20 in accordance with the present invention. The strap 20 of FIGS. 4 and 5 is provided with extension strap 12, buckle 13 with hook 14, and securing strap 15 as before.

However, as best seen in FIG. 6 the strap 20 is provided with an inflatable base strap 21 which is preferably formed from fabric covered rubber such as is used in inflatable air beds. The base strap 21 is therefore hollow and is provided with a stopper 22 through which air can be introduced into, and extracted from, the interior 23 of the base strap 21. This is preferably done by blowing exhaled air into the interior 23.

Figure 7:
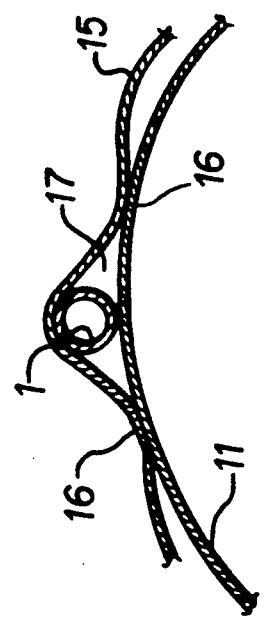
FIG. 7 is a perspective view of a patient illustrating how three of the splints of FIGS. 1 to 3 can be utilized together with straps as illustrated in FIG. 4 in order to splint a fractured femur.
Figure 8:
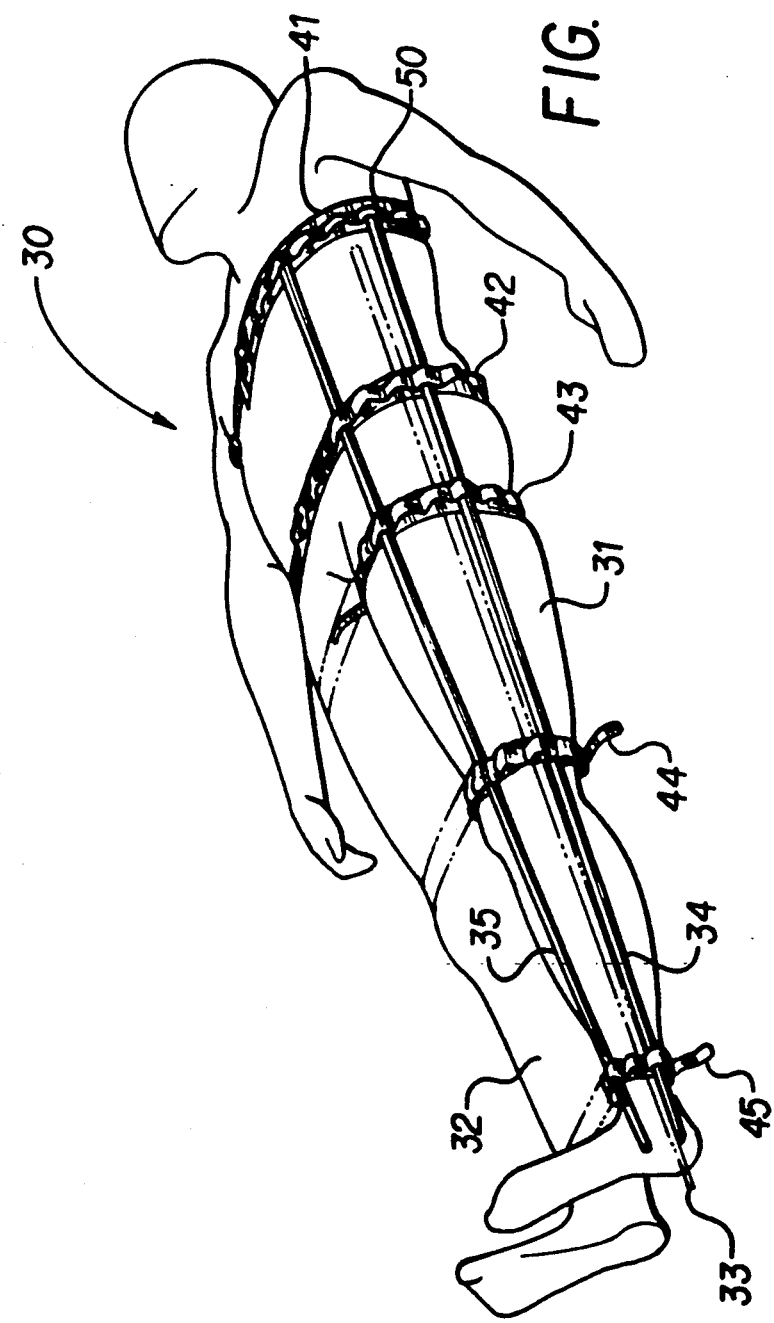
FIG. 8 is a view illustrating a splint of FIG. 7 in cross-section passing through one of the splint securing straps.

FIGS. 7 and 8 illustrate how the apparatus of FIGS. 1 to 3 is used to splint a patient having a broken femur. The patient 30 has his left leg 31 broken at the femur (not illustrated). If necessary the left leg 31 is straightened and the right leg 32 placed alongside as illustrated in FIG. 7. Three splints 33, 34 and 35 are placed into the operational configuration illustrated in FIG. 1. Five of the straps 10 illustrated in FIG. 3 and designated 41 to 45 are loosely placed around the body of the patient 30 in the positions illustrated. Thus strap 41 is placed around the upper chest, strap 42 is placed around the waist, strap 43 is placed around the upper thigh of the fractured left leg 31, strap 44 is placed around the knee of the left leg 31 and strap 45 is placed around the ankle of the left leg 31.

The three splints 33-35 are then slid through selected ones of the apertures 17 so as to lie in the positions illustrated in FIG. 7. In these positions, the three splints 33-35 very approximately lie at the vertices of an imaginary triangle which is a substantially equilateral triangle. It will be appreciated in this connection that the splint 33 passes between the ankle and below the back of the patient 30 approximately below the shoulder blade, splint 34 passes between the ankle and the armpit of the patient, while splint 35 passes between the ankle and the left nipple of the patient 30.

Whilst the straps 41-45 were loosely located in the position illustrated in FIG. 7 by engagement of the respective hooks 14 with a selected one of the apertures 17; after the splints 33-35 have been positioned, the straps 41-45 can be tightened by pulling the free ends of the extension straps 12. This action firmly braces the three splints 33-35 around the left leg 31 and thus immobilizes the leg, particularly against rotation. The patient 30 is then able to be transported from the site where the fracture occurred, to hospital.

As illustrated by dotted lines in FIG. 7, the straps 43-45 can be passed around both the left leg 31 and the right leg 32 so as to clamp both legs of the patient 30 together, if this is desirable for the particular nature of the patient's injuries.

As also illustrated in FIG. 7, the ends of the splints 33-35 adjacent the patient's armpit can be retained within the pocket 50 provided on strap 41. Straps 42-45 are not required to have the pocket 50 but if the pocket 50 is provided the splints 33-35 pass over these pockets.

FIG. 8 illustrates in a cross-sectional view, how the splint 1 passes between the base strap 11 and the securing strip 15.

It will be apparent to those skilled in the first aid arts, that the strap 20 of FIGS. 4 and 5 can be used in substantially the same way as the strap 10 of FIG. 3 however, additional, or alternative, tightening of the strap 20 can be achieved by inflating the interior 23.

Figure 9:
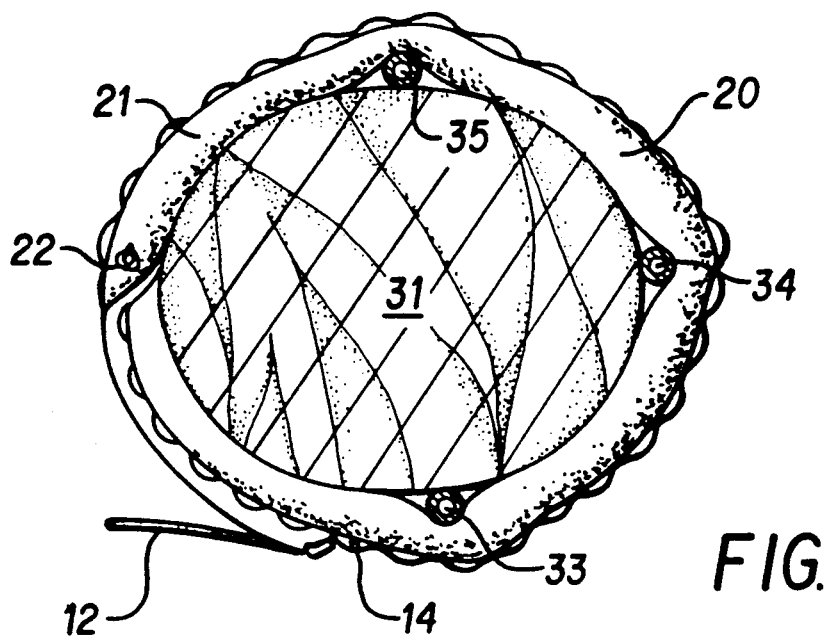
FIG. 9 is a transverse cross-sectional view through a limb illustrating one method of using the inflatable splint securing strap of FIGS. 5 and 6.

An alternative arrangement of using the straps 20 is illustrated in FIG. 9. Here the splints 33-35 are arranged around the leg 31 in the same manner as illustrated in FIG. 7, however, each of the straps 20 in this embodiment is located outside of the splints 33-35 prior to inflation of the base strap 21. When the base strap 21 is inflated, the situation illustrated in FIG. 8 is reached in which the inflated base strap 21 holds the splints 33-35 in position.

It will be apparent from FIG. 9 that the splints 33, 34 and 35 lie approximately at the vertices of a triangle which is preferably a substantially equilateral triangle.

In this way the splints 33-35 securely brace the leg 31 against movement and particularly against rotation about the longitudinal axis of the leg 31.

Figure 10:
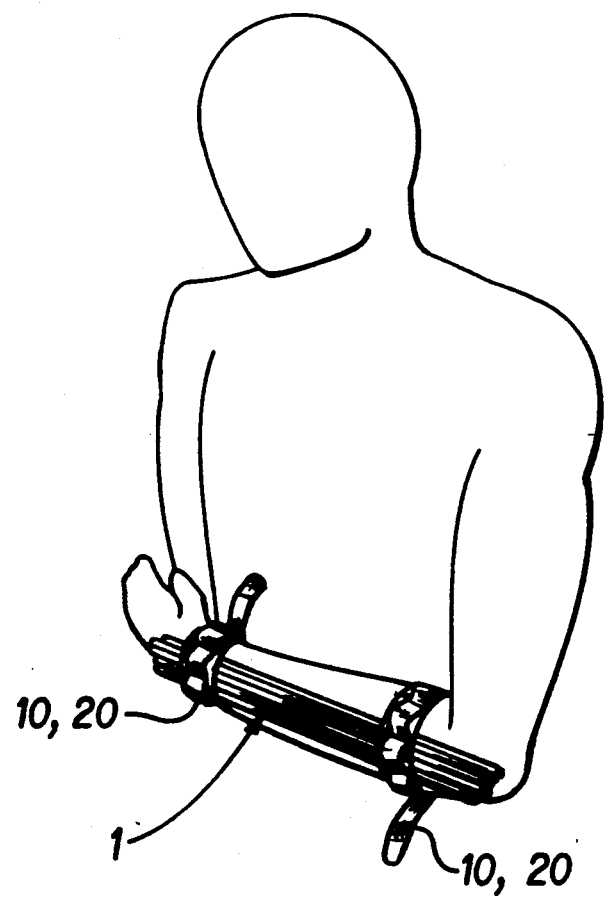
FIG. 10 is a perspective view of a patient having a broken forearm splinted by means of the splint of FIGS. 1 to 3 and the strap of FIG. 4.
Figure 11:
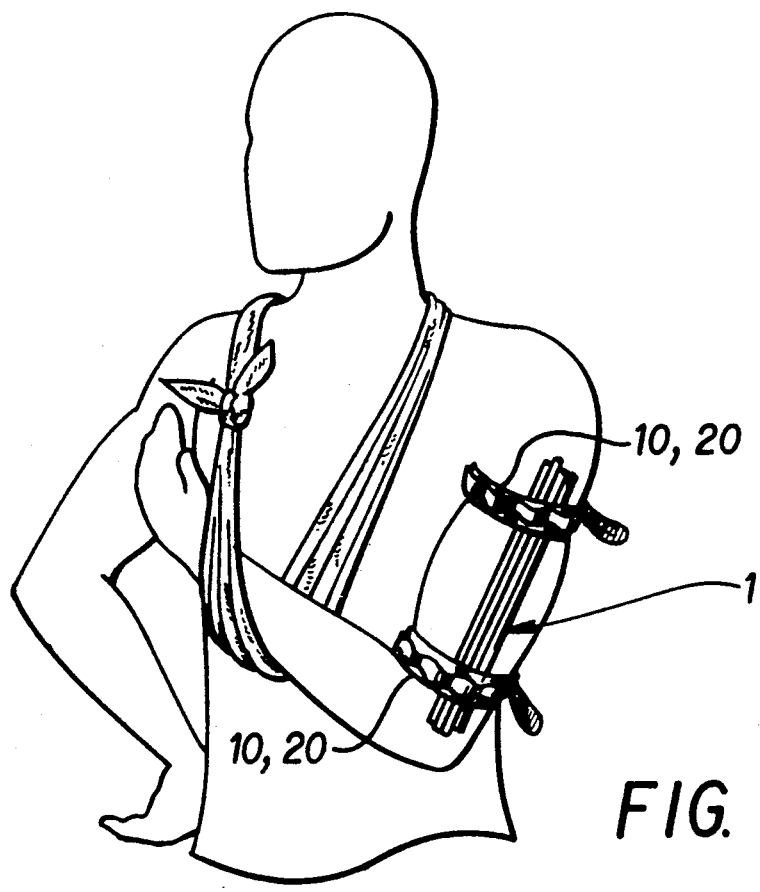
FIG. 11 is a perspective view of a patient having a fractured upper arm splinted using the apparatus of FIGS. 1 to 4.
Figure 12:
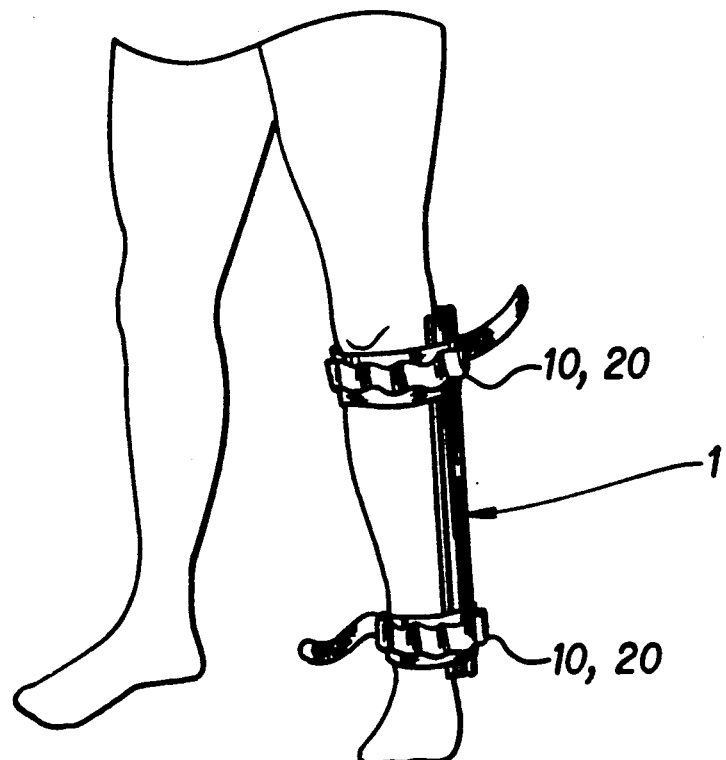
FIG. 12 is a view similar to FIG. 10 but illustrating one possible splinting of the lower leg.

FIGS. 10 to 12 respectively illustrate how the splint 1 and straps 10, 20 can be used to splint a broken forearm, a broken upper arm and a broken lower leg respectively. For each of these injuries, the overall length of the splint 1 as illustrated in FIG. 1 is not required. Therefore the splint 1 can be either folded in half, or in quarters as illustrated in FIG. 2 and used as appropriate for the length of the broken portion of the limb. If desired, the splint 1 can pass through a selected aperture 17 as illustrated in FIG. 8 or, alternatively, as illustrated in FIGS. 10 to 12, the splint 1 can be located intermediate the broken limb and the strap 10, 20.

Figures 13, 14:
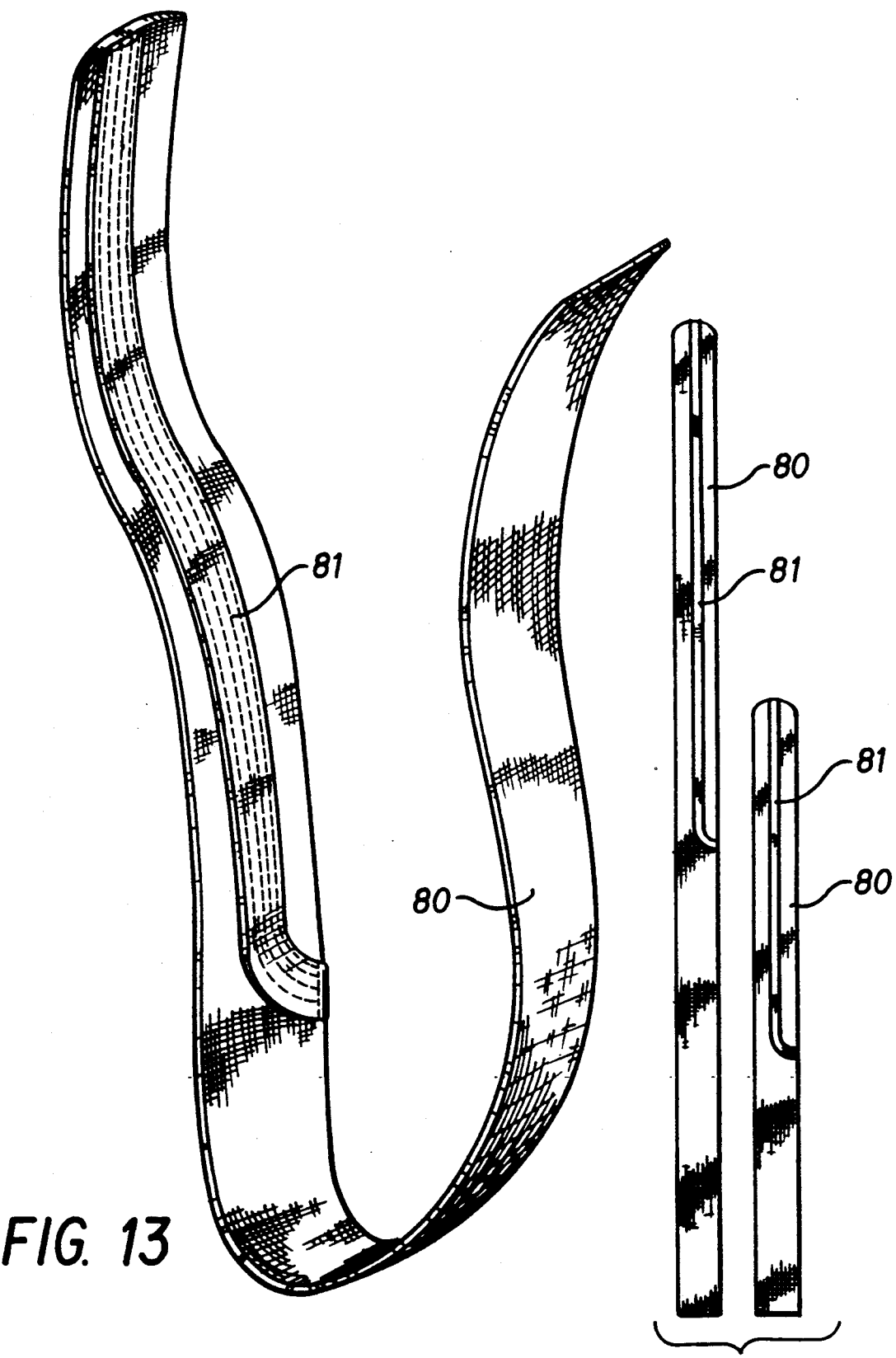
FIG. 13 is a perspective view of a third embodiment of a splint securing strap.
FIG. 14 is a plan view of the strap of FIG. 13 and a similar, but longer strap.
Figure 15:
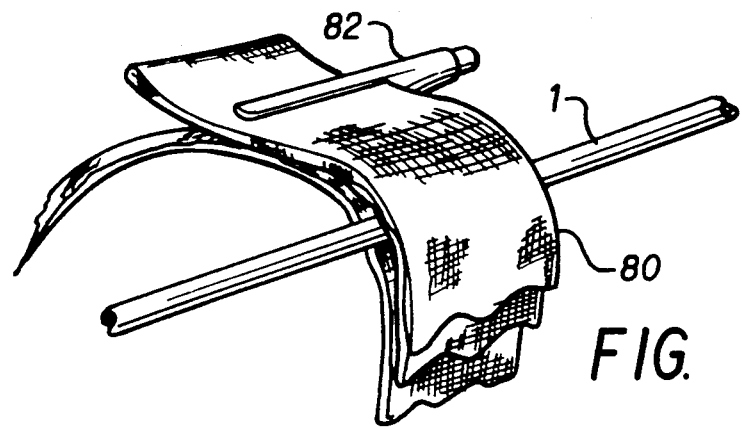
FIG. 15 is a schematic perspective view showing how the straps of FIGS. 13 and 14 can be secured by means of a peg.

A still further strap 80 is illustrated in FIGS. 13 and 14. This strap is formed from a length of neoprene foam. A strip 81 of fabric is sewn along the strap 80 for a portion of its length in order to reduce its elasticity. As illustrated in FIG. 15 the straps 80 can be wrapped around a splint 1 and secured by a peg 82. Because the strap 80 is able to be stretched to a substantial extent the degree of firmness of the strap's binding about the patient is determined by the degree of extension of the strap 80.

Figure 16:
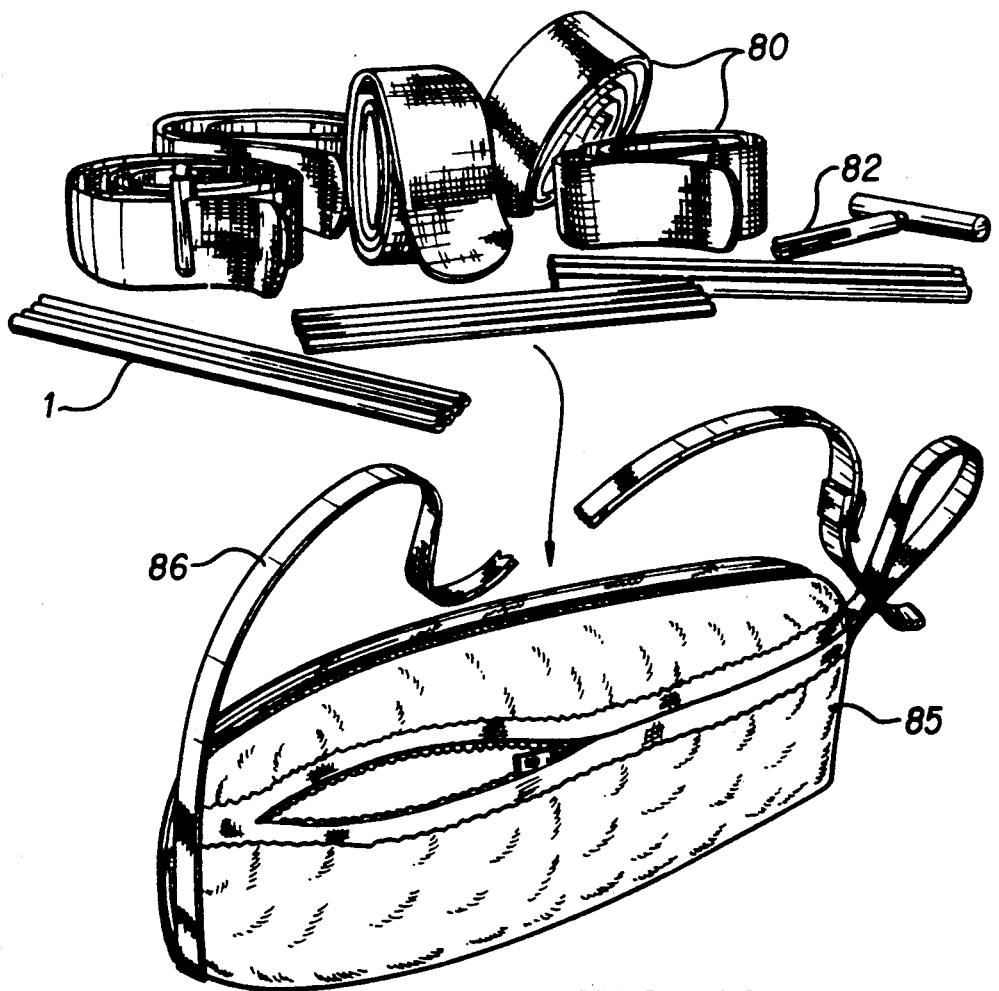
FIG. 16 is a perspective view of straps of the embodiment of FIGS. 13-15 which together with splints and pegs can be placed into a first aid bag.

As illustrated in FIG. 16, a plurality of straps 80, pegs 82 and splints 1, is able to be located within a convenient carry pouch or bag 85 having a shoulder strap 86.

Figure 17:
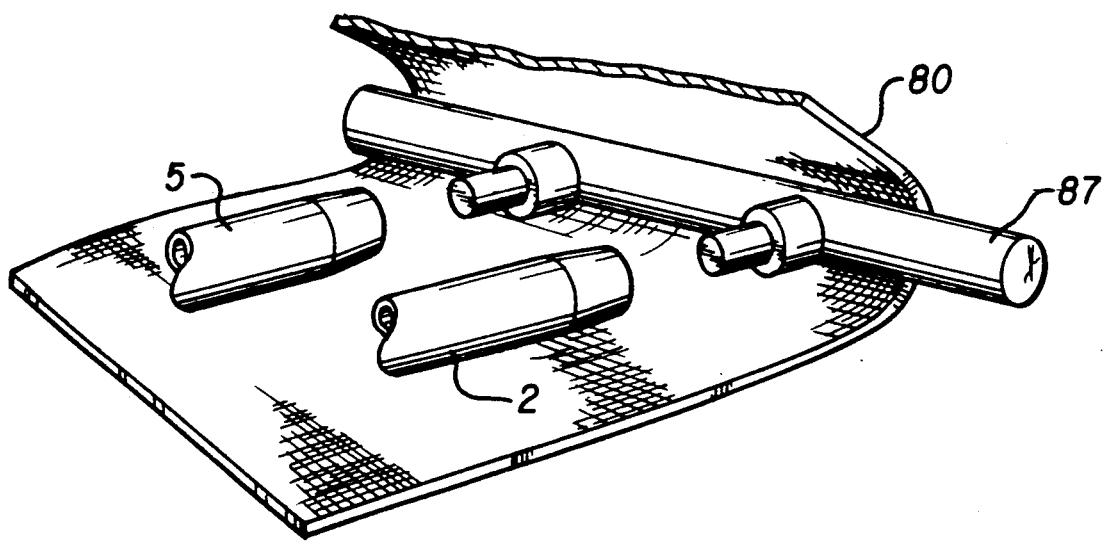
FIG. 17 is a schematic perspective view showing how two splint end tubes can be connected to a cross bar for pushing straps under a patient.

Turning now to FIG. 17, it will be appreciated that it is sometimes difficult to pass the straps 10, 20 or 80 underneath a patient without disturbing him and therefore possibly causing further injury. In order to overcome this problem the ends 8 of the opposite end tubes 2 and 5 (FIGS. 1-3) are shaped to releasably engage a cross piece 87 (FIG. 17). A strap 80, for example, is located over the cross piece 87 as illustrated in FIG. 17 and then pushed under the patient by pushing the ends 2, 5 of the splint 1 (in its folded in half configuration) under the patient. After the strap 80 has been pushed through, it can then be grasped from the other side. At this stage the splint 1 can be withdrawn from under the patient and returned to its extended configuration shown in FIG. 1.

This procedure can be used to locate the straps 80 in FIG. 18 underneath the patient during each turn of the strapping procedure. FIG. 19 illustrates an alternative form of arranging the four tubes 2-5 during splinting of the lower leg so as to better immobilize it against rotation.

Figure 20:
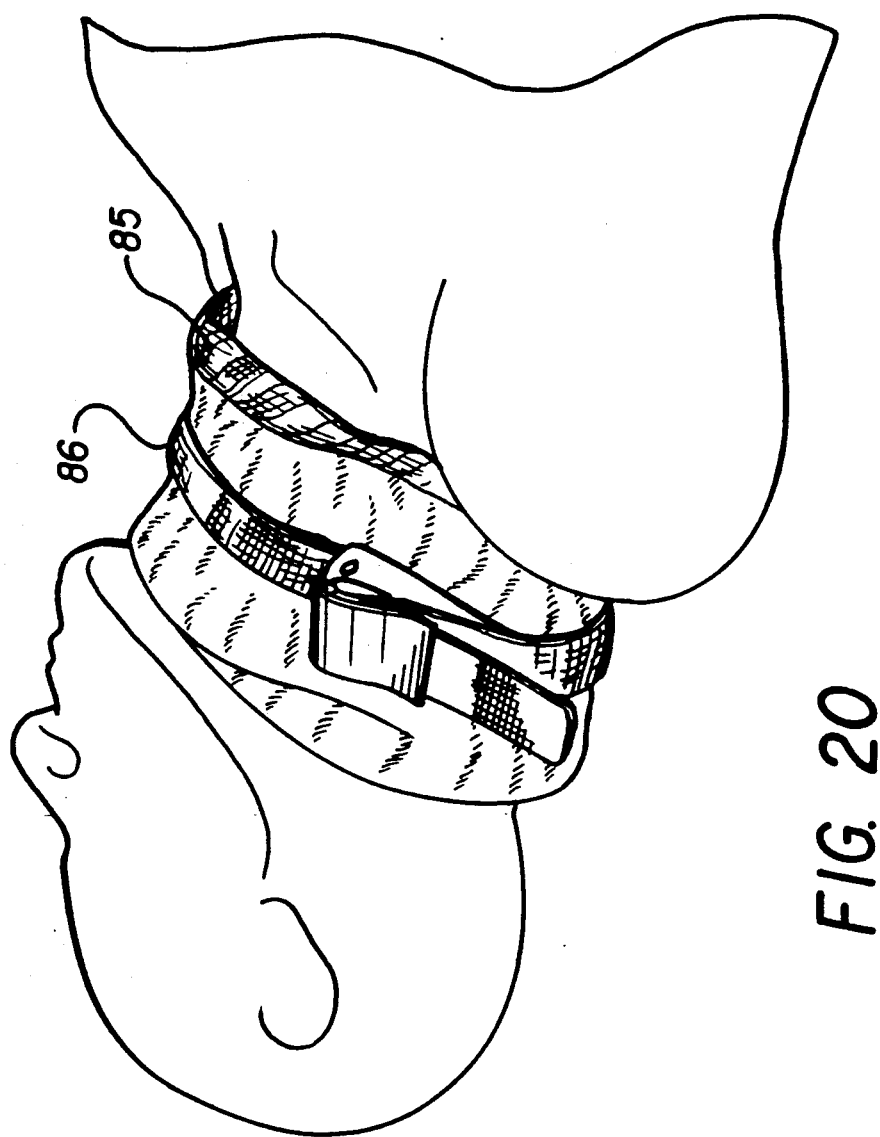
FIG. 20 is a perspective view illustrating how the bag of FIG. 16 can be used as a neck brace.

Turning now to FIG. 20, in the event of a neck injury such as whiplash or broken neck vertebra, it is possible to wrap the bag 85 around the patient's neck and secure it in place as a temporary neck brace using the carry strap 86.

As illustrated in FIG. 7 in relation to strap 41, it is particularly desirable for the strap adjacent the patient's armpit to have a pocket 50. The purpose of the pocket 50 in relation to the patient's armpit is best understood in relation to FIGS. 21 and 22 which illustrate an ankle tensioning strap. One problem with broken femurs is that it is highly desirable that the leg which is broken be retained in longitudinal tension. This prevents the natural contraction of the muscles drawing the broken ends of the bone towards each other and sliding past each other.

Figures 21, 22:
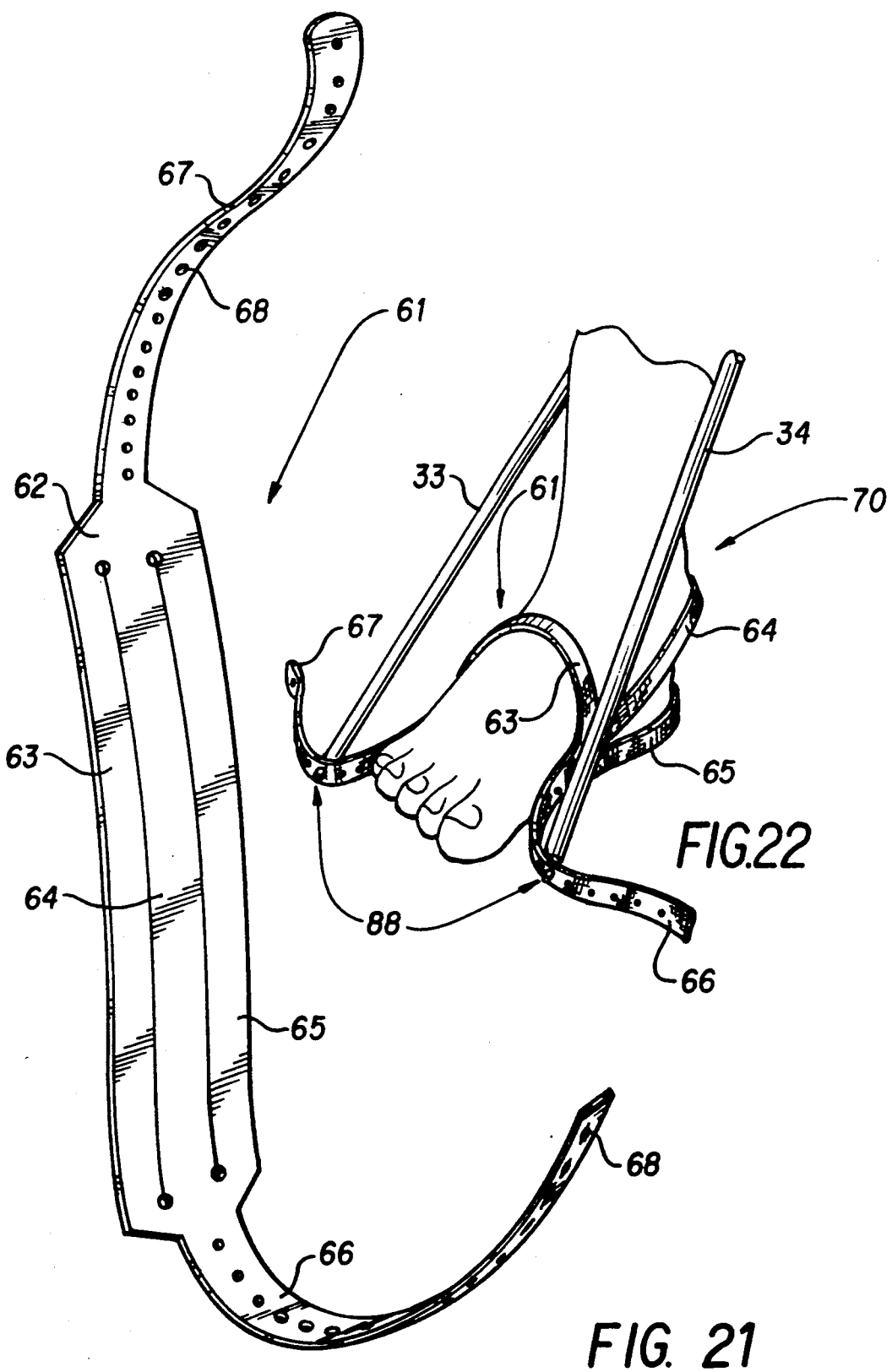
FIG. 21 is a perspective view of an ankle tensioning strap.
FIG. 22 is a perspective view of the strap of FIG. 21 in use.

As seen in FIG. 21, the ankle tensioning strap 61 is provided with a center portion 62 split into three bands 63-65. The center portion 62 is also provided with two extensions 66 and 67 at opposite ends thereof. The extensions 66, 67 are each provided with a series of holes 68.

As seen in FIG. 22, the ankle tensioning strap 61 is able to be passed over the ankle 70 of the patient's broken leg. One of the bands 63 passes over the upper surface of the patient's foot, whilst the center band 64 passes towards the rear of the heel of the patient's foot and engages with the skin in the region of the Archilles tendon. The remaining band 65 is either unengaged or engages the "corner" between the sole and the heel.

With the ankle tensioning strap 61 so arranged relative to the ankle of the patient, the extensions 66, 67 are then stretched and a selected one of the holes 68 on each of the extensions 66, 67 is engaged with the free ends of the splints 33, 34. A pin 88 can be used for this purpose.

Since the ankle tensioning strap 61 is preferably made from rubber impregnated fabric, the strap 61 exhibits a substantial degree of resilience. As a consequence, by stretching the extensions 66, 67 and securing same relative to the splints 33, 34 then the center band 64, in particular, draws the ankle 70 of the patient away from the patient's hip.

Naturally, the force exerted on the patient's ankle 70 by means of the ankle tensioning strap 61 results in an equal and opposite force being applied to the splints 33, 34. This force is easily able to be overcome since the other end of the splints 33, 34 is restrained against such a force by means of the pocket 50 as illustrated in FIG. 7. The strap 41, for example, including the pocket 50 is easily able to be immobilized by being tightened around the patient's chest.

It will be apparent that FIG. 22 is somewhat schematic in that the third splint 35 of FIG. 6 is not illustrated in FIG. 22 since only two splints 33, 34 are required for the tensioning process. It will be apparent to those skilled in the art however, that the ankle tensioning strap 61 illustrated in FIG. 17 is preferably used in place of the strap 45 illustrated in FIG. 7. In this way, the leg 31 of the patient 30 in FIG. 7 can be maintained under longitudinal tension for the duration of the period in which the patient's leg is splinted.

INDUSTRIAL APPLICATION

It will be apparent that the above described arrangements have many advantages. The splints are able to be readily assembled and disassembled and transported in a compact configuration. Similarly, the straps are able to be rolled into a compact ball when not in use. Although a kit of such splints and straps is able to splint broken femurs it is also able to splint other broken limbs and thus has wide application for both civilian and military first aid use. Furthermore, the apparatus can be used at night by sense of touch alone since there is no ambiguity of construction.

The foregoing describes only some embodiments of the present invention and modifications, obvious to those skilled in the art, can be made thereto without departing from the scope of the present invention.

We claim:

1. A method of splinting a patient having a leg with a fracture of the femur, said method comprising the steps of straightening said leg if necessary, positioning three substantially rigid splints to extend between substantially the ankle of said leg and the armpit region of said patient, arranging said splints to be at the vertices of a triangle when said leg is viewed in transverse cross-section, and securing said splints so arranged to the body of said patient.

2. A method as claimed in claim 1 wherein said splints are secured by passing a plurality of straps around said splints and patient and tightening said straps, said straps being positioned at longitudinally spaced locations along the patient's body.

3. A method as claimed in claim 2 wherein one of said straps passes around the chest of said patient, a second of said straps passes around the waist of said patient, a third of said straps passes around the thigh of said leg or around both thighs of said patient, a fourth of said straps passes around the knee of said leg or around both knees of said patient, and a fifth of said straps passes around the ankle of said leg or around both ankles of said patient.

4. A method as claimed in claim 2 wherein one of said straps is secured around the chest of said patient and includes restraining means to restrain the longitudinal movement of at least two of said splints towards the head of said patient, and the ankle of said leg is resiliently secured to said at least two splints to urge said ankle away from said head to thereby place said leg in longitudinal tension.

5. A method as claimed in claim 2, 3 or 4 wherein at least one of said straps secured around the patient has a hollow portion which is at least partially inflated with a fluid.

* * * * *